US006436143B1

(12) United States Patent
Ross et al.

(10) Patent No.: US 6,436,143 B1
(45) Date of Patent: Aug. 20, 2002

(54) METHOD AND APPARATUS FOR TREATING INTERVERTEBRAL DISKS

(76) Inventors: Anthony C. Ross, 4928 Palace Pleasant Lake, Hollywood, SC (US) 29349; Peter A. Guagliano, 379 Bay Ridge Pkwy., Brooklyn, NY (US) 11709

( * ) Notice: Subject to any disclaimer, the term of this patent is extended or adjusted under 35 U.S.C. 154(b) by 0 days.

(21) Appl. No.: 09/569,807

(22) Filed: May 12, 2000

Related U.S. Application Data

(63) Continuation-in-part of application No. 09/456,375, filed on Dec. 8, 1999, which is a continuation-in-part of application No. 09/274,217, filed on Mar. 23, 1999, which is a continuation-in-part of application No. 09/255,372, filed on Feb. 22, 1999.

(51) Int. Cl.[7] .................................................. A61F 2/44
(52) U.S. Cl. ........................ 623/17.16; 606/94; 606/99; 604/38
(58) Field of Search ........................... 623/16.11, 17.16, 623/8, 66; 606/61, 86, 99, 92–94; 604/38, 95.03

(56) References Cited

U.S. PATENT DOCUMENTS

| | | | | |
|---|---|---|---|---|
| 3,890,970 A | * | 6/1975 | Gullen | 604/170.02 |
| 4,000,741 A | * | 1/1977 | Binard et al. | 604/121 |
| 4,265,618 A | | 5/1981 | Herskovitz et al. | |
| 4,357,136 A | | 11/1982 | Herskovitz et al. | |
| 4,517,326 A | * | 5/1985 | Cordts et al. | 523/113 |
| 4,648,880 A | * | 3/1987 | Brauman | 623/8 |
| 4,651,717 A | * | 3/1987 | Jakubczak | 128/899 |
| 4,723,547 A | * | 2/1988 | Kullas et al. | 606/185 |
| 4,820,303 A | * | 4/1989 | Brauman | 623/8 |
| 4,944,749 A | * | 7/1990 | Becker | 623/8 |
| 4,966,583 A | * | 10/1990 | Debbas | 604/98 |
| 5,047,055 A | * | 9/1991 | Bao et al. | 623/17 |
| 5,183,463 A | * | 2/1993 | Debbas | 604/98 |
| 5,445,645 A | * | 8/1995 | Debbas | 606/192 |
| 5,545,229 A | | 8/1996 | Parsons et al. | |
| 5,549,679 A | * | 8/1996 | Kuslich | 623/17 |
| RE35,391 E | * | 12/1996 | Brauman | 623/8 |
| 5,632,777 A | * | 5/1997 | Petrick | 623/11 |
| 5,656,013 A | * | 8/1997 | Yoon | 600/207 |
| 5,662,674 A | * | 9/1997 | Debbas | 606/192 |
| 5,800,549 A | * | 9/1998 | Bao et al. | 623/17 |
| 5,865,802 A | * | 2/1999 | Yoon et al. | 604/104 |
| 6,183,518 B1 | * | 2/2001 | Ross et al. | 623/17.16 |
| 6,206,921 B1 | * | 3/2001 | Guagliano et al. | 623/17 |
| 6,241,734 B1 | * | 6/2001 | Scribner et al. | 606/93 |

\* cited by examiner

*Primary Examiner*—Jeffrey A. Smith
*Assistant Examiner*—Michael B. Priddy
(74) *Attorney, Agent, or Firm*—Browning Bushman P.C.

(57) ABSTRACT

The method and apparatus as shown in FIGS. 8–10 in which a fluid expandable member (208) is positioned in concentric relation about a needle (202). The fluid expandable member (208) is expanded into the nucleus pulposus potential space bordered by the annulus fibrosus of an intervertebral disk. Then, thermoplastic material in a flowing state is injected by a needle (202) within the annulus fibrosus to collapse the fluid expandable member (208) and occupy the space formerly occupied by the fluid expandable member (208).

18 Claims, 6 Drawing Sheets

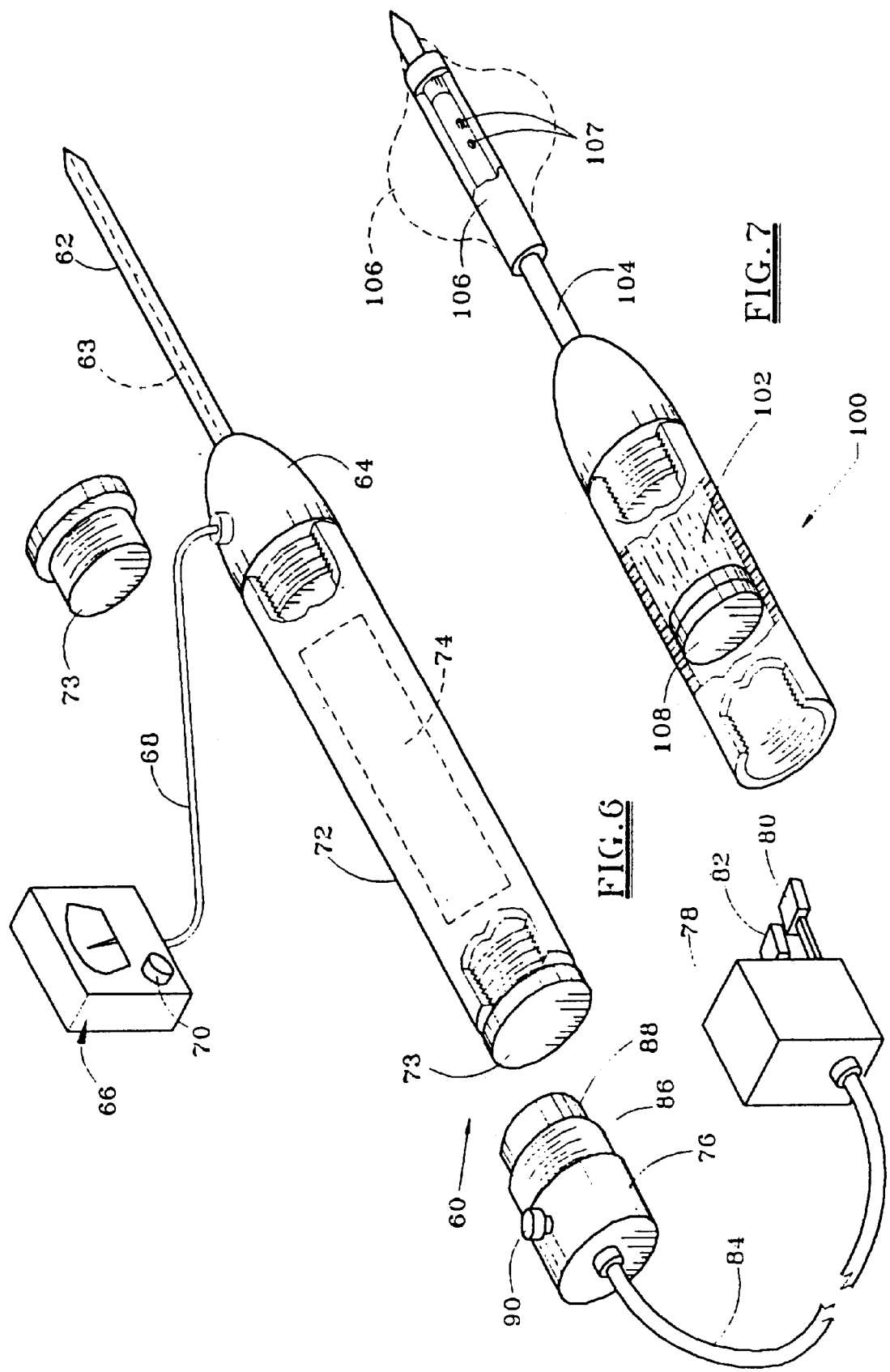

METHOD AND APPARATUS FOR TREATING INTERVERTEBRAL DISKS

CROSS REFERENCE TO RELATED APPLICATIONS

This is a continuation-in-part of pending application Ser. No. 09/456,375 filed Dec. 8, 1999; which is a continuation-in-part of application Ser. No. 09/274,217 filed Mar. 23, 1999; which is a continuation-in-part of application Ser. No. 09/255,372 filed Feb. 22, 1999.

FIELD OF THE INVENTION

This invention relates to surgical methods generally, and is more specifically related to a method and apparatus for treating intervertebral disks of mammals.

BACKGROUND OF THE INVENTION

The intervertebral disk is a disk with fibrosus bands occupying the space between two vertebrae. The anatomy of the disk provides a cushion to allow motion, limit motion and provide space, distancing the vertebra off the nerves and compressible tissue. Part of the vertebrae are bony blocks, which, when stacked one upon the other, form the anterior portion of the spine. The fibrosus band includes an outer annulus fibrosus which surrounds an inner nucleus pulposus. Annulus fibrosus, as referred to herein, is the marginal or peripheral portion of an intervertebral disk. Intervertebral disks are prone to injury. Due to the low blood supply to this area, intervertebral disks are slow to heal, and may not materially heal. When the annulus fibrosus is torn, or punctured, the nucleus pulposus can leak or migrate from the annulus fibrosus. The nucleus pulposus is a substance of jelly like consistency found in the center of an intervertebral disk and flows from the associated annulus fibrosus when the annulus fibrosus is ruptured or prolapsed.

The effect of a ruptured or prolapsed annulus fibrosus may result in spasm, and neurological compromise, such as the compressed nerve and other compressible soft tissues, i.e. arteries, veins. Degeneration of the condition may increase over time, resulting in chronic and debilitating pain. The condition is usually disabling.

Suppressive measures include steroidal injection, removal of the nucleus pulposus, and fusion either by donor bone, coral or by metal bracing. If disk removal is performed, a healthy part of the disk is often taken, eradicating the function of the joint, and accelerating the degeneration of adjacent segments of the body, as the body attempts to stabilize. This approach frequently leaves the patient immunologically and structurally compromised if not permanently disabled.

Isolated treatment to only the damaged structures employing the most non-invasive procedure possible is preferred. This approach allows as much of the healthy tissue as possible to remain, and to retain normal neurological function. While the offending material can be removed, the material must be replaced with a material which will perform the function formerly performed by the material removed. A need exists for a process which limits the material removed from the intervertebral disk, and which replaces the material so removed with a composition that is physiologically acceptable to the human body, and which allows the intervertebral disk to retain motion and characteristics of normal joint function, including cushioning the joint as compression is introduced from the stacking of the vertebrae. The thermoplastic material must be pliable in its application, and non-flowing after replacement.

In addition, many patients suffer from scoliosis or lateral curvature of the spine. The most common remedy at the present time is the fusion normally by donor bone or metal bracing which oftentimes is not successful or only partially successful. Pain normally accompanies scoliosis and pain suppressants may result in an undesirable chemical dependency in some instances. A need exists to correct the abnormal curvature of the spine without utilizing fusion techniques applied to the spine.

SUMMARY OF THE INVENTION

The present invention is particularly directed to a process for treating the spine including the injection of a thermoplastic material heated to a predetermined temperature for injection into the nucleus pulposus in a flowing state where it cools and sets at body temperature into a non-flowing state. Inorganic materials have been shown to penetrate the endplates of the associated vertebrae. A thermoplastic or thermoplastic polymer material is any plastic or organic material that softens when heated and hardens when cooled. The thermoplastic material prior to injection is heated to a temperature sufficient for the material to flow under pressure into the nucleus pulposus and, after it sets into a non-flowing state at body temperature, the material retains sufficient resilience to provide desired cushioning of the spine.

A thermoplastic material which has been found to be highly satisfactory is gutta percha which is normally combined with other elements or ingredients in a suitable gutta percha compound. Gutta percha is a linear crystalline polymer which melts at a predetermined temperature a random but distinct change in structure results. Normal body temperature is 37 C and a suitable thermoplastic material hardens into a non-flowing state at a temperature range between about 35 C and 42 C (the degree symbol for temperature is omitted in all references herein to a specific temperature). A crystalline phase appears in two forms; an alpha phase and a beta phase. The alpha form is the material that comes from the natural tree product. The processed form is the beta form. When heated, gutta percha undergoes phase transitions. When there is a temperature increase, there is a transition from beta phase to alpha phase at about 46 C. The gutta percha changes to an amorphous phase about 54 C to 60 C. When cooled very slowly, about 1 C per hour, the gutta percha crystallizes to the alpha phase. Normal cooling returns the gutta percha to the beta phase. Gutta percha softens at a temperature above about 64 C. A suitable gutta percha compound is dental gutta percha which contains by weight only about 20% gutta percha with zinc oxide comprising about 60% to 75% of the material. The remaining 5% to 10% consists of various resins, waxes, and metal sulfates. The percentages listed are directed to an optimum gutta percha compound. The preferred percentage of gutta percha is in the range of 15% to 40%. Zinc oxide and metals in the gutta percha compound are desirable for imaging such as X-rays while resins and waxes are desirable for obtaining an adequate flow of the thermoplastic material. Gutta percha provides the desired resiliency at body temperature and is at least about 15% of the compound. Zinc oxide also provides an anti-inflammatory property. In some instances, a mineral trioxide aggregate may be added to the gutta percha compound.

An injection device, such as an injection gun, is utilized for heating and injecting the thermoplastic material under a predetermined pressure within the spine. The injection device may utilize a silver needle, encased in ceramics, of about 20 to 30 centimeters in length with a diameter as high as 1 centimeter. The size of the needle may depend on such factors as the amount of thermoplastic material to be injected, the temperature of the thermoplastic being injected, and the axial pressure applied by the injection device, such as a piston or plunger, to the thermoplastic material to force the heated material from the end of the needle into the spine. The thermoplastic material is physiologically acceptable to the human body.

When the thermoplastic material is utilized to treat a ruptured annulus fibrosus, the nucleus pulposus is removed and the material removed is replaced by the heated thermoplastic material which sets at body temperature and provides sufficient resilience after setting to permit adequate motion and cushioning of the vertebrae. The cushioning effect of the gutta percha compound provides a semimobile disk as a buffer to a fusion to reduce the possibility of sequential iatrogenic disk degeneration. The thermoplastic material is injected within the potential nucleus pulposus space bordered by the annulus fibrosus to replace the removed nucleus pulposus by a needle of the injection device.

When the thermoplastic material is injected within the spine to reduce a scoliosis, the material is sequentially injected by a needle of the injection device into the annulus fibrosus or interannular at the apex and adjacent joints of the concavity of the scoliosis. Such an injection tends to straighten the curvature of the spine is a wedge-like action.

An embodiment illustrated in FIGS. 8–10 includes an injection system in which an expandable member is first expanded into the annulus fibrosus of a disk and then a thermoplastic material is injected into the annulus fibrosus to collapse the expandable member and occupy the space formerly occupied by the expandable member. The expandable member is mounted in concentric relation about the needle.

It is an object of the present invention to provide a method of injecting a thermoplastic material into the annulus fibrosus of a spine.

A further object of the present invention is to provide such a method in which the thermoplastic material is heated to a predetermined temperature for flow into the annulus fibrosus and hardens when it cools from body temperature into a non-flowing state to form a resilient support for cushioning between vertebrae.

Another object of the invention is to provide a method to treat a ruptured annulus fibrosus of a spine by removal of the nucleus pulposus and injection of a thermoplastic material into the annulus fibrosus to replace the nucleus pulposus.

An additional object is to provide an apparatus to treat an annulus fibrosus of a spine in which an injection device heats the thermoplastic material for flow into the annulus fibrosus and another injection member is effective for expanding an expandable member in the annulus fibrosus.

Other objects, features, and advantages of the invention will be apparent from the following specification and drawings.

BRIEF DESCRIPTION OF THE DRAWINGS

FIG. 6 is a perspective view of a modified injecting device for injecting a thermoplastic material within the spine;

FIG. 7 is a perspective view of a disk dilator;

DETAILED DESCRIPTION OF THE PREFERRED EMBODIMENTS

Figure 1:
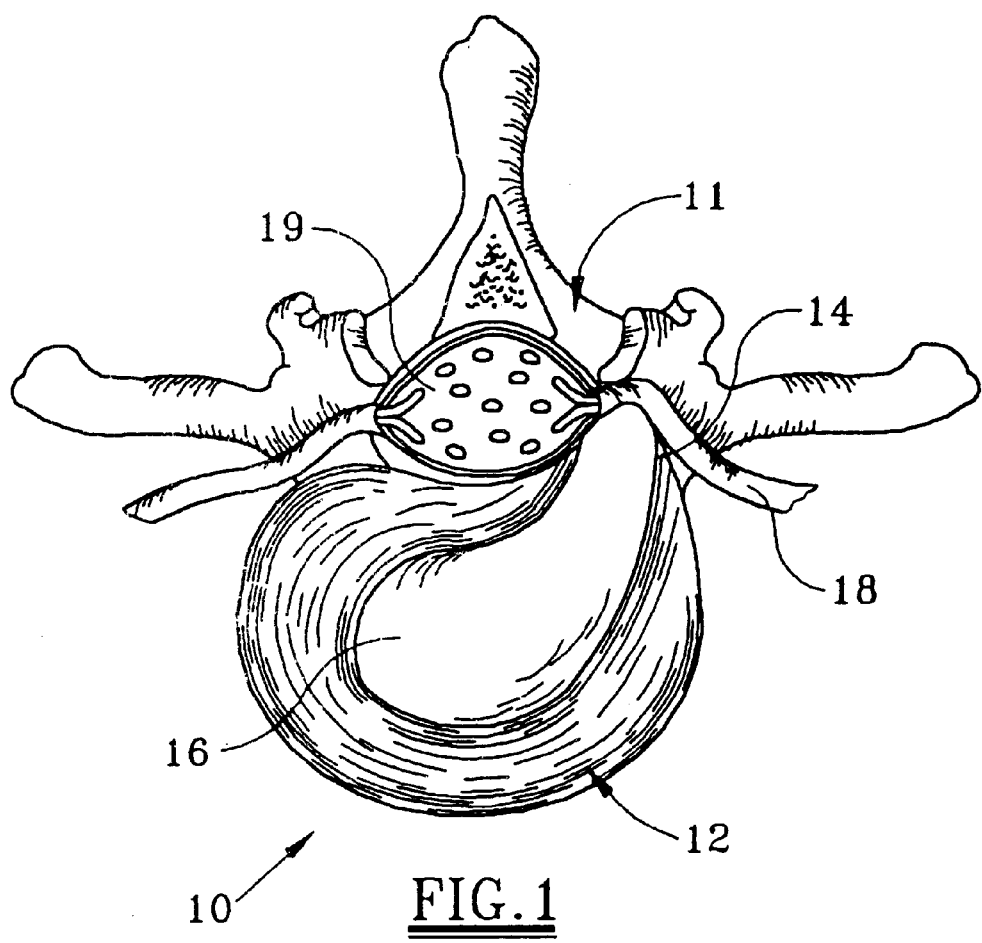
FIG. 1 is a diagrammatic view of a ruptured/prolapsed annulus fibrosus and the resulting migrated nucleus pulposus of an intervertebral disk.
Figure 2:
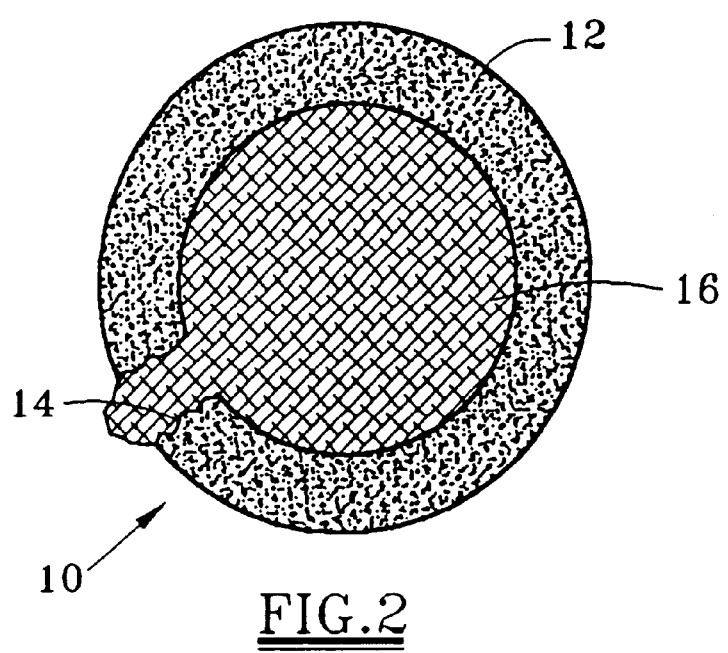
FIG. 2 is a sectional view of the ruptured annulus fibrosus showing leakage of the nucleus pulposus.

Referring now to the drawings for a better understanding of the invention, and more particularly to the embodiment shown in FIGS. 1–4, a portion of a spine is shown generally pictorially in FIG. 1 including an intervertebral disk 10 adjacent a vertebra 11. Disk 10 has an annulus fibrosus 12 which has ruptured at 14 resulting in a leakage or migration of nucleus pulposus 16 from the annulus fibrosus 12. In this example a sacral nerve is shown at 18 extending from the cauda eqina 19 and the migrating or flowing nucleus pulposus 16 may result in a compression of nerve 18 with recognition that the techniques will be adapted specific to facilitate delivery to different levels of the spine.

It is desired to remove nucleus pulposus 16 which flows at body temperature and replace it with a thermoplastic material which does not flow at body temperature (37 C). FIGS. 1–4 illustrate the removal of the nucleus pulposus 16 and replacement with a thermoplastic material. For this purpose the rupture or prolapse of the annulus fibrosus 12 is first identified and isolated. This identification and isolation is by means such as X-ray, MRI or other diagnostic imaging procedures which are diagnostically acceptable. After the area of rupture or prolapse is identified and isolated the site is surgically accessed. Since it is a goal of the invention to minimize trauma associated with the procedure, it is preferred to access the site through an arthroscopic procedure, or technology that involves minimal invasion and offense to healthy areas of the annulus fibrosus 12, while damaged parts of the intervertebral disk are removed. Current technology allows for surgical removal of nucleus pulposus 16 by irrigation and suction.

The nucleus pulposus 16 removed is replaced with a thermoplastic material which is physiologically acceptable to the human body and flows when injected but hardens at body temperature into a non-flowing resilient material. The thermoplastic material is first heated by a suitable injection device having an injection needle to a predetermined temperature for flow under pressure from the needle into the annulus fibrosus 12 wherein the nucleus pulposus 16 has been removed. A thermoplastic material which has been found to be highly satisfactory is gutta percha or a gutta percha compound. Gutta percha is a geometric isomer of natural rubber. A substance such as mineral trioxide aggregate and other anti-inflammatory elements may be added to the gutta percha to facilitate the binding properties and to facilitate healing of the affected area. Dental gutta percha which may be utilized contains approximately 20% gutta percha, with zinc oxide comprising 60% to 75% of the material. The remaining 5% to 10% consists of various resins, waxes, metal sulfates for radioopacity, and coloration. When cold, gutta percha is relatively inelastic, but as it warms it becomes moldable. At a high temperature gutta percha will flow under pressure to permit injection from an injection needle into the annulus fibrosus 12.

Figure 3:
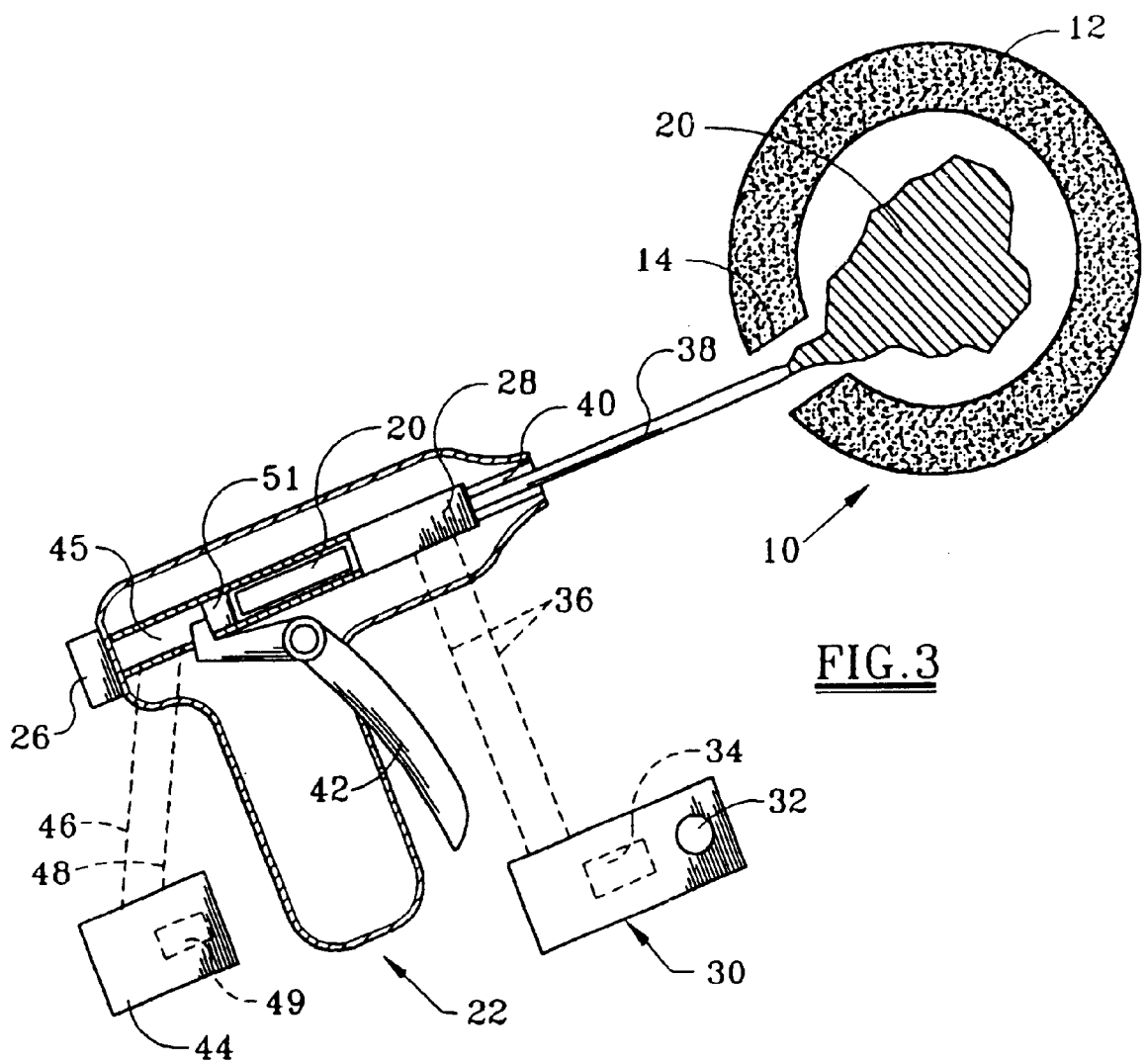
FIG. 3 is a diagrammatic view illustrating injection of a thermoplastic material by an injecting device into the annulus fibrosus for replacement of the nucleus pulposus.
Figure 4:
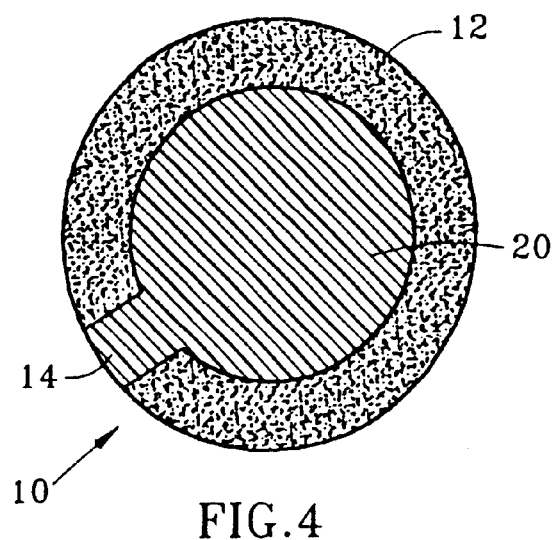
FIG. 4 shows the intervertebral disk after setting of the thermoplastic material.

Referring particularly to FIG. 3, injection of thermoplastic material 20 within the annulus fibrosus 12 by an injection device or gun illustrated schematically at 22 is shown. Injection gun 22 has a body 24 with a removable plunger 26 adapted to receive a cylindrical plug of the thermoplastic material 20. A heater 28 is provided to heat the thermoplastic material 20 and a heater control unit 30 having an adjustable temperature control knob 32 is provided with a temperature readout at 34. Electrical leads 36 extend to heater 28. An injection needle 38 preferably formed of silver extends from body 24 and has a ceramic sheath 40 about a portion of needle 38. A hand operated trigger 42 may be activated for forcing thermoplastic material 20 from the end of needle 38 upon heating of the thermoplastic material 20 to a predetermined temperature. To assist trigger 42 in exerting an axial force against the plug of thermoplastic material 20 in gun 22, a foot operated hydraulic pump may be provided at 44 to supply fluid through lines 46, 48 to a hydraulic cylinder 45. A pressure readout is provided at 49. A suitable piston 51 may exert an axial force against the thermoplastic material 20. A hydraulic system is effective in providing an axial injection force that may be easily regulated and controlled by personnel performing the procedure. A suitable injection device designated as a Obtura II Heated Gutta Percha System may be purchased from Obtura of Fenton, Mo.

Needle 38 preferably formed of silver may be of various diameters but will not exceed a diameter of about 1 centimeter. Needle 38 may have a length of between 20 centimeters and 30 centimeters. A plug or stick of the thermoplastic material 20 may have a total volume of about 21 cubic centimeters with a diameter of about 16 millimeters and a length of about 10½ centimeters. The thermoplastic material 20 is required to be heated prior to injection to permit flow of the thermoplastic material. The higher the temperature of the thermoplastic material, the lower the viscosity and the faster flow. A lower temperature heating increases the viscosity and retards the flow rate. The degree to which the thermoplastic material 20 is heated may vary substantially dependent primarily on the diameter of needle 38 and the axial force applied to the heated thermoplastic material for injection. Generally the lowest temperature to which the thermoplastic material is heated while utilizing a large diameter needle such as 1 centimeter in diameter with a relatively high axial force may be 50 C while the highest temperature will be less than about 250 C.

The optimum temperature is about 185 C within an optimum range between about 150 C and 200 C.

It is desirable for the thermoplastic material to have a viscosity and temperature suitable for injection and flow into the space previously occupied by the annulus fibrosus 12. After injection of the thermoplastic material 20 into the annulus fibrosus 12, the material flows to fill the entire void area of the annulus fibrosus possibly including the ruptured area 14. The thermoplastic material 20 cools relatively rapidly and, for example, reaches body temperature about its outer surface very quickly if injected at a temperature of about 185 C and then cools internally to body temperature in several minutes depending primarily on the thickness and surface area of the thermoplastic material. The thermoplastic material 20 tends to set at about 42 C and is not in a flowing state lower than about 42 C. Upon reaching the body temperature of 37 C, the thermoplastic material is set. At normal human body temperature the thermoplastic material is no longer moldable and is not flowing or migrating. Thus, the thermoplastic material 20 remains within the annulus fibrosus 16 and repairs the rupture 14 of the annulus fibrosus. It is, however, necessary that the thermoplastic material retain sufficient resilience in order to provide in a satisfactory manner the functions of allowing motion and adequately cushioning of the joint between associated vertebrae. If necessary, the thermoplastic material 20 may be subsequently removed from the annulus fibrosus 12 by surgical, physical, enzymatic, and/or chemical means.

Figure 5:
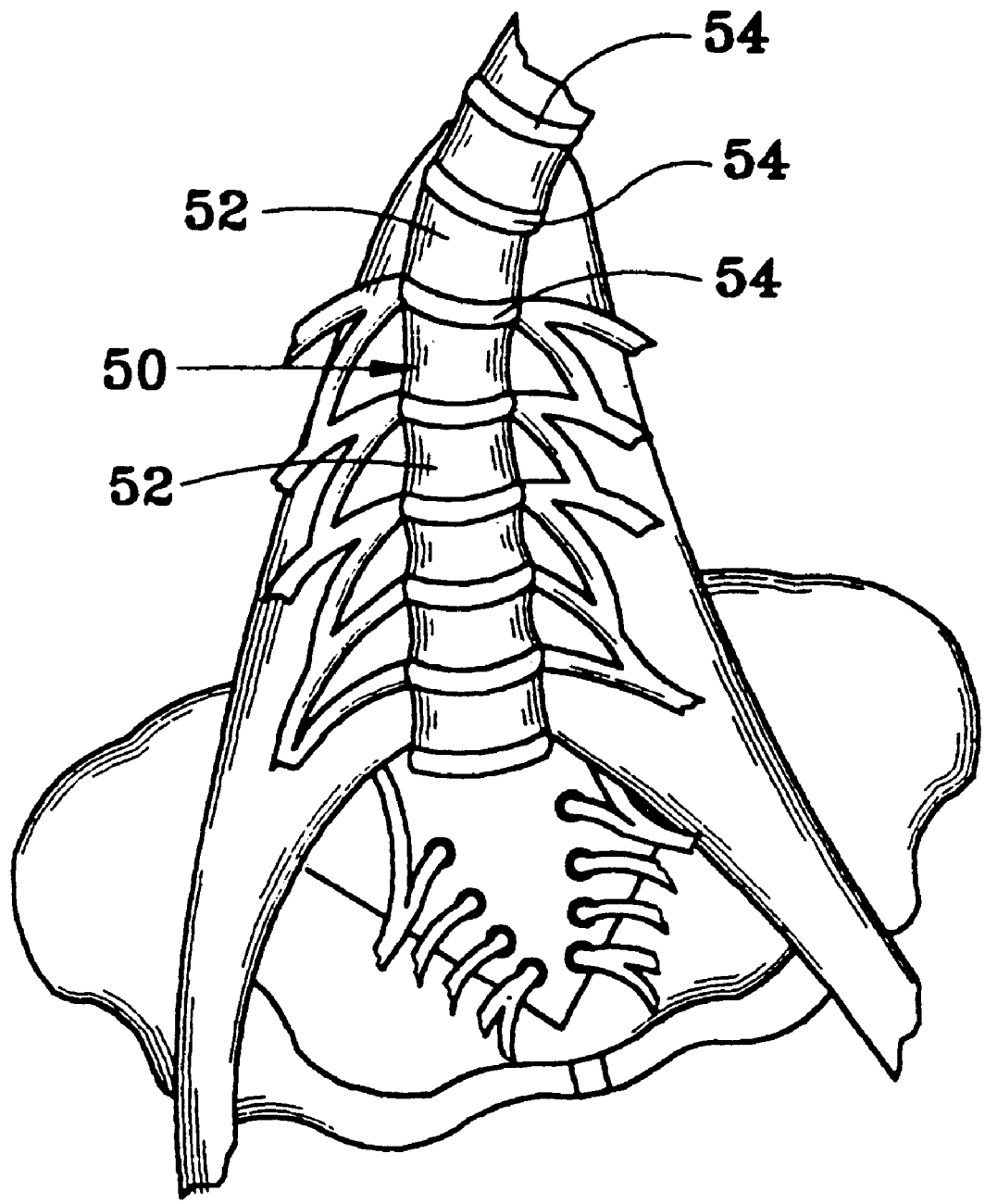
FIG. 5 illustrates the abnormal curvature of the lower spine for the injection of a thermoplastic material into the curved concave portion of the spine.

Referring now to FIG. 5, a spinal column is shown generally at 50 having vertebrae 52 with intervertebral disks 54 positioned therebetween. FIG. 5 shows spine 50 with scoliosis or abnormal curvature of the spine. The abnormal curvature of spine 50 provides a concave curvature as shown in FIG. 5 at which disks 34 are positioned. To correct or remedy the abnormal curvature of spine 50, a thermoplastic material 20 may be injected at intervertebral disks 54 progressively to reduce the concavity for flow into the associated annulus fibrosus as in the procedure set forth in FIGS. 1–4. The amount of the injected material will vary with the greatest amount of injected material at the greatest deflection and the least amount at the disks closest to the terminal ends of the abnormal curvature. However, the nucleus pulposus is not removed from the spine 50. The injected material provides a force acting as a wedge to reduce the concavity of the scoliosis. Gutta percha as set forth in the embodiment of FIGS. 1–4 is the preferred material for the thermoplastic material to be injected due to the characteristics that allow gutta percha to be used in other joints of the body.

Embodiment of FIG. 6

Referring to FIG. 6, a modified injection device is shown generally at 60 including an injection needle 62, a heater 64 receiving an inner end portion of needle 62, and an electrical heater control element 66 having leads 68 extending to heater 64. A suitable control knob 70 controls the temperature and a readout panel indicates the temperature which, for example, may be about 185 C.

A generally cylindrical chamber or housing 72 adjacent heater 64 is provided to receive a cylindrical plug 74 of the thermoplastic material. Housing 72 has open ends to receive removable threaded end plugs 73 for maintaining plug 74 in a sealed relation. One plug 73 is shown removed from housing 72 in FIG. 6. Plug 74 may also be covered with a suitable cover which may be manually removed for use, either in combination with or without end plugs 73. Housing 72 upon removal of plugs 73 may be connected to heater 64 at one end and connected to a fluid pressure chamber 76 at an opposed end. A suitable fluid from a reservoir 78 having a foot operated pedal 80 and a vent 82 is supplied through line 84 to pressure chamber 76. Concentric pistons 86 and 88 responsive to pressurized fluid in chamber 76 are provided to engage the end of thermoplastic plug 74 to urge plug 74 into heater 64 for injection from needle 62 under a predetermined pressure. A pressure gauge 90 is provided to indicate the fluid pressure applied against thermoplastic plug 74. In some instances, housing 72 may be disposable with heater 64 being of an increased length to receive the entire length of plug 74.

Needle 62 is preferably about 6 mm in diameter, and between about 20 cm and 30 cm in length for maneuverability. The volume of thermoplastic material to purge needle 62 may be between about 5.65 cc and 8.48 cc dependent on the size of the needle. Approximately 15 cc of thermoplastic material may be utilized for injection within the spine. Cylindrical plug 74 may have a total volume of 21 cc with a diameter of 16 mm and a length of 10.45 cm to provide a compact unit.

It may be desirable in some instances to provide a heater tape 63 in needle 62 for heating of the projecting needle 62. Needle 62 may be formed of a ceramic material and preferably includes an inner silver liner for receiving heater tape 63 which may be formed of a suitable material to provide an electrical resistance, for example. Needle 62, heater 64 and housing 72 may comprise separate injection subassemblies removably connected to pressure chamber 76 by a suitable threaded connection thereby to provide disposable units if desired with leads 68 detached from heater 64. The fluid for the hydraulic system for fluid cylinder 76 may be water or another innocuous fluid.

Embodiment of FIG. 7

Also shown in FIG. 7 as an attachment is a disk dilator assembly generally indicated at 100 having a cylindrical chamber 102 with an inert fluid such as saline therein and a piston 108 for pressurizing the fluid. Disk dilator assembly 100 is designed for detachable connection to pressure chamber 76 of the injector device of FIG. 6 for the supply of hydraulic fluid for acting against piston 108. A detachable balloon dilator sleeve 106 extends about the extending end of needle 104 having lateral openings 107. Piston 108 is effective to pressurize the fluid for flow through openings 107 for expansion of sleeve 106 as shown in broken lines in FIG. 7. Dilator sleeve 106 upon injection of needle 104 in a disk of the spine is expanded for exerting an expanding force against the disk.

Figure 8:
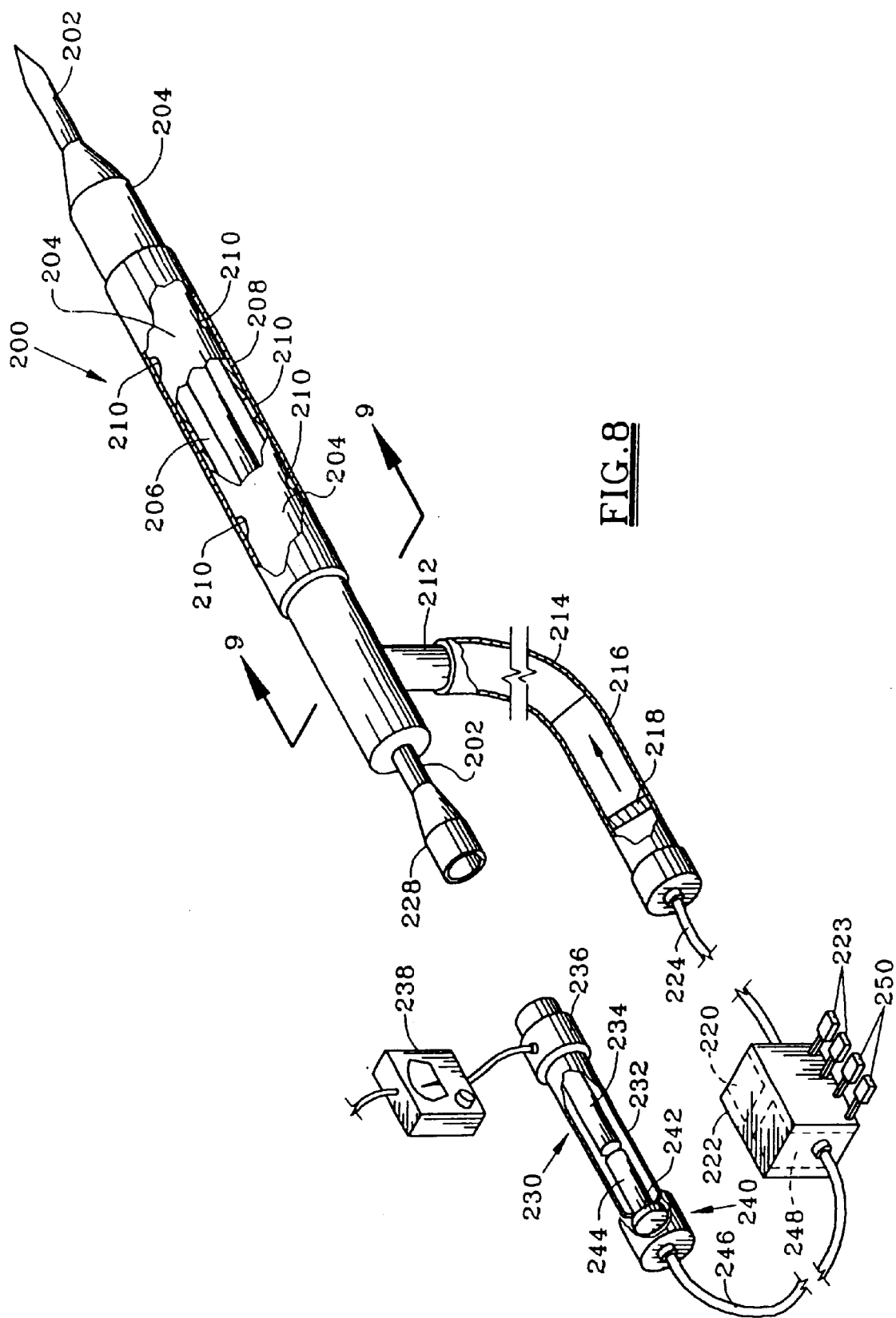
FIG. 8 is a generally schematic view of a separate embodiment of the invention in which a disk dilator is intentionally provided to force adjacent disks apart and then a thermoplastic material is injected in the space occupied by the expandable dilator member.
Figure 9:
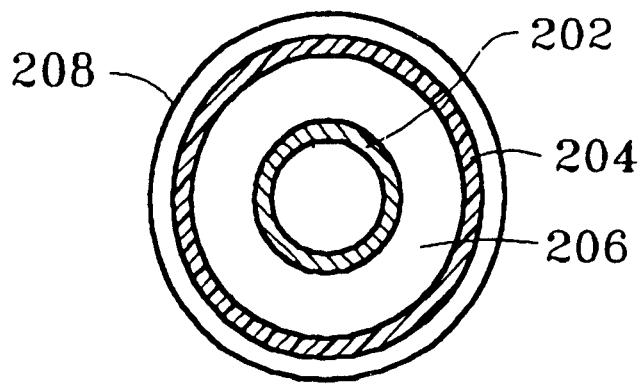
FIG. 9 is a section taken generally along line 9—9 of FIG. 8.
Figure 10:
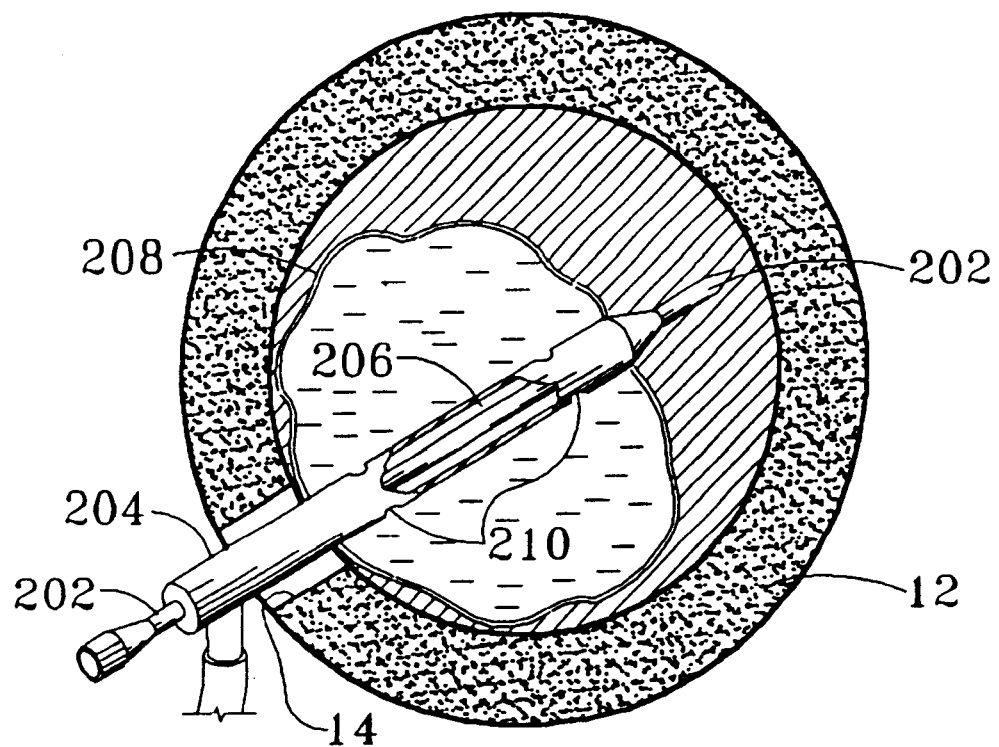
FIG. 10 is a sectional view of an annulus fibrosus showing the expandable member expanded and the injection of the thermoplastic material adjacent the expandable member.

Embodiment of FIGS. 8–10

Referring now to FIGS. 8–10 which are partially schematic, a further modification of an injection device and injection system is illustrated utilizing certain features shown in the embodiments of FIGS. 6 and 7. The injection system shown generally in FIG. 8 includes an injection device generally indicated at 200 having an inner needle 202 and an outer concentric sheath or housing 204 forming an annulus 206 therebetween. An outer dilator sleeve 208 is mounted about sheath 204. Openings 210 in the wall of sheath 204 permit fluid flow from annulus 206 through openings 210 for expansion of dilator sleeve 208. Dilator sleeve 208 may be formed of an inert elastomeric material.

As shown in FIG. 10, annulus fibrosus 12 has a rupture 14 therein. Fluid such as a saline solution is first injected through annulus 206 and openings 210 to expand sleeve 208 in the void area of the annulus fibrosus 12 for forcing adjacent vertebrae apart. After the vertebrae have been forced apart and expandable sleeve 208 fits tightly against the surface defining the void area, a gutta percha compound is injected through needle 202 to fill the area occupied by expandable sleeve 208. The pressure at which the gutta percha is injected is greater than the pressure of the saline solution to force the saline solution from sleeve 208 to collapse sleeve 208. If desired, the pressure of the saline solution may also be decreased.

After insertion of the gutta percha compound, injection device 200 may be withdrawn from the annulus fibrosus 12. Gutta percha is injected at pressures generally between about 10 psi and 150 psi dependent primarily on the size of the patient, such as infants requiring a very low psi and a relatively large person requiring a relatively high psi.

The system for injection of the saline solution and gutta percha as shown in FIG. 8 includes a branch connection 212 extending from sheath 204 and connected to a flexible hose 214. A cylindrical chamber 216 for saline or other suitable sanitary liquid fills chamber 216, hose 112, and annulus 206. A piston 218 is mounted in chamber 216. Hydraulic fluid in reservoir 220 of tank 222 is dispensed by operation of suitable foot pedals 223 and other suitable controls. The hydraulic fluid through hose 224 acts against piston 218 for pressurizing chamber 216 and forcing saline through openings 210 for expanding sleeve 208 against the surface defining the void area in annulus fibrosus 12.

Hollow needle 202 is connected to a flexible hose 228 extending to a gutta percha injection device 230 generally similar to injection device 60 shown in FIG. 6. Gutta percha device 230 includes a cylindrical chamber or housing 232 having a plug 234 of gutta percha therein. A heater 236 is controlled by electrical control panel 238 having suitable electrical controls thereon. A hydraulic cap 240 mounted within the end of cylinder 232 has a pair of telescoping pistons 242, 244 for engaging gutta percha plug 234 and forcing the heated gutta percha through the end of needle 202 into the annulus fibrosus 12 as shown in FIG. 10 to force expanding sleeve 208 to a collapsed position with gutta percha filling the entire void area in the annulus fibrosus 12. Hydraulic fluid line 246 extends to a fluid reservoir 248 in tank 222 and foot pedals 250 may be operated for pressurizing and venting hydraulic cap 240 and chamber 232. Thus, expanding sleeve 208 is effective in defining the void area upon the expansion of sleeve 208. Then, the gutta percha easily flows into the area formed by expanding sleeve 208. Expanding sleeve 208 is also effective in forcing adjacent disks apart and the increased area or volume is also filled with gutta percha thereby making the gutta percha more effective in filling the void area of the annulus fibrosus 12.

The injection system shown in FIGS. 8–10 is generally a combination of the embodiments shown in FIGS. 6 and 7. The housing and expandable sleeve shown in FIG. 7 may befitted about the hollow needle of FIG. 6 and saline for expanding the sleeve may be provided through a "y" adapter to the annulus between the needle and the housing. Thus, the system shown in FIGS. 8–10 comprises a combination of the features shown in the embodiment of FIGS. 6 and 7.

While gutta percha or a gutta percha compound including at least about 15% of the compound by weight is the preferred thermoplastic material, it is understood that other types of thermoplastic material may be suitable if in a non-flowing state at body temperature (37 C) and in a flowing state when heated over at least about 50 C for injection from a needle of an injection device. Various other ingredients or elements may be added to the gutta percha compound in various percentages. Further, while specific injection devices have been illustrated for injection of the thermoplastic material, other types of injection devices for heating the thermoplastic material and for applying an axial force against the thermoplastic material for injection may be provided. For example, various devices may be provided for heating the thermoplastic material prior to injection and for pressurizing the thermoplastic material for controlled flow of the thermoplastic material through an injection needle for injection. Thus, while preferred embodiments of the present invention have been illustrated in detail, it is apparent that modifications and adaptations of the preferred embodiments will occur to those skilled in the art. However, it is to be expressly understood that such modifications and adaptations are within the spirit and scope of the present invention as set forth in the following claims.

What is claimed is:

1. A method for treating an intervertebral disk of the spine, comprising:

selecting an intervertebral disk of the spine;

providing an injection device having an expandable member about an injection needle for a thermoplastic material;

injecting said expandable member and said needle into the annulus fibrosus of said selected disk;

expanding said expandable member into the annulus fibrosus of said selected disk; and then injecting a thermoplastic material from said needle into said annulus fibrosus of said selected disk to occupy the space defined by said expandable member.

2. The method defined in claim 1, further comprising:

injecting said thermoplastic material from said needle under a pressure greater than the pressure for expanding said expandable member to effect collapsing of said expandable member with said thermoplastic material occupying the space formerly occupied by said expandable member.

3. The method defined in claim 1, further comprising:

removing nucleus pulposus from said annulus fibrosus prior to insertion of said expandable member and said needle into said annulus fibrosus.

4. An injection device for treating an intervertebral disk of the spine of a patient, comprising:

a hollow needle for the injection of a thermoplastic material into the annulus fibrosus of a disk from the projecting end of the needle;

an expandable member about said hollow needle for expanding into the annulus fibrosus of the disk prior to injection of the thermoplastic material in the annulus fibrosus; and a heater for heating said thermoplastic material to effect flowing thereof prior to injection into the annulus fibrosus.

5. An injection system for treating an intervertebral disk of a spines comprising:

an injection device including a hollow needle for injecting a thermoplastic material within the annulus fibrosus of a disk, and an expandable member about said hollow needle to form an annulus between said needle and said expandable member;

a fluid pressure device to provide pressurized fluid in said annulus for expanding said expandable member into said annulus fibrosus;

a heating device for heating the thermoplastic material; and a force applying device for forcing said thermoplastic material from said needle in a flowing state.

6. The injection system as defined in claim 5, further comprising:

a concentric sleeve about said needle for forming said annulus between said sleeve and said needle, said expandable member mounted about said sleeve.

7. The injection system as defined in claim 6 wherein said sleeve has a plurality of openings therein for communicating fluid to said expandable member for expanding said expandable member within said annulus fibrosus.

8. The injection system as defined in claim 5 wherein said fluid pressure device includes a pressurized liquid, and a hydraulically actuated piston for pressurizing said liquid.

9. An injection gun for injecting a thermoplastic material between a joint of a patient, comprising:

a chamber for receiving said thermoplastic material in a non-flowing state;

a heater adjacent said chamber for heating said thermoplastic material to a flowing state;

a hollow injection needle operatively connected to said heater to receive the flowing thermoplastic material from said heater for injection between the joint of the patient; and a hydraulic force applying assembly to apply hydraulic force against said thermoplastic material to force the thermoplastic material when heated to a flowing state from said needle.

10. The injection gun as defined in claim 9, further comprising:

a plug of said thermoplastic material within said chamber, said hydraulic force applying assembly including a hydraulically actuated piston adjacent said plug for forcing said thermoplastic material from said needle after said thermoplastic material is heated to a flowing state.

11. The injection gun as defined in claim 10, further comprising:

a fluid pressure source for said hydraulically actuated piston; and a foot operated pedal associated with said fluid pressure source to provide a selected fluid pressure to said piston and heated thermoplastic material.

12. The injection gun as defined in claim 9, further comprising:

an expandable member about said hollow needle to form an annulus between said needle and said expandable member; and a fluid pressure device to provide pressurized fluid in said annulus for expanding said expandable member.

13. The injection gun as defined in claim 9, further comprising:

a substantially rigid concentric sleeve about said hollow needle for forming an annulus between said sleeve and said needle;

an expandable member mounted about said sleeve; and a fluid pressurization device to provide pressurization fluid in said annulus for expanding said expandable member, said expandable member being in fluid communication with said annulus.

14. The injection gun as defined in claim 9, wherein said thermoplastic material comprises gutta percha.

15. The injection gun as defined in claim 9, wherein said thermoplastic material comprises a gutta percha compound in which gutta percha is between 15% and 40% by weight of the compound.

16. The injection gun as defined in claim 9, wherein said heater heats said thermoplastic material compound for flowing at a temperature between about 150 C and 200 C.

17. The injection gun as defined in claim 9, further comprising:

a generally cylindrical housing forming the chamber to receive a plug of thermoplastic material and having opposed open ends, said cylindrical housing being removable from said injection needle; and a threaded end plug for each of said open ends when said housing is removed from said injection needle for sealing of said thermoplastic material therein.

18. The injection device as defined in claim 17, wherein said heater is removably mounted adjacent one of said open ends upon removal of an associated end plug.

* * * * *

UNITED STATES PATENT AND TRADEMARK OFFICE
CERTIFICATE OF CORRECTION

PATENT NO. : 6,436,143 B1
DATED : August 20, 2002
INVENTOR(S) : Ross et al.

It is certified that error appears in the above-identified patent and that said Letters Patent is hereby corrected as shown below:

<u>Column 9,</u>
Line 38, change "splines" to -- spline --.

Signed and Sealed this

Thirty-first Day of December, 2002

JAMES E. ROGAN
*Director of the United States Patent and Trademark Office*